(12) United States Patent
Oh

(10) Patent No.: US 9,421,148 B2
(45) Date of Patent: *Aug. 23, 2016

(54) INTEGRATED INFUSION CONTAINER

(75) Inventor: Gi-Bum Oh, Seoul (KR)

(73) Assignee: BNCP CORPORATION, Closter, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/400,852

(22) Filed: Feb. 21, 2012

(65) Prior Publication Data

US 2013/0218122 A1 Aug. 22, 2013

Related U.S. Application Data

(63) Continuation of application No. 11/994,186, filed as application No. PCT/KR2006/002522 on Jun. 28, 2006, now Pat. No. 8,128,612.

(30) Foreign Application Priority Data

Jun. 28, 2005 (KR) .......................... 10-2005-0056511

(51) Int. Cl.
| | |
|---|---|
| *A61M 5/00* | (2006.01) |
| *A61J 1/00* | (2006.01) |
| *A61J 1/10* | (2006.01) |
| *A61J 1/20* | (2006.01) |

(52) U.S. Cl.
CPC ................ *A61J 1/10* (2013.01); *A61J 1/2089* (2013.01); *A61J 1/1418* (2015.05); *A61J 1/201* (2015.05); *A61J 1/2065* (2015.05); *A61J 2001/201* (2013.01); *A61J 2001/2065* (2013.01)

(58) Field of Classification Search
CPC ............... A61M 5/31596; A61M 2005/31598
USPC .................................................. 604/414, 416
See application file for complete search history.

(56) References Cited

U.S. PATENT DOCUMENTS

| | | | | |
|---|---|---|---|---|
| 4,410,321 A | * | 10/1983 | Pearson et al. | 604/520 |
| 4,467,588 A | * | 8/1984 | Carveth | 53/425 |
| 4,583,971 A | * | 4/1986 | Bocquet et al. | 604/82 |
| 4,589,879 A | * | 5/1986 | Pearson | 604/411 |
| 4,606,734 A | * | 8/1986 | Larkin et al. | 604/84 |
| 4,645,073 A | * | 2/1987 | Homan | 206/219 |
| 4,936,841 A | * | 6/1990 | Aoki et al. | 604/413 |
| 5,061,264 A | * | 10/1991 | Scarrow | 604/408 |
| 5,088,996 A | * | 2/1992 | Kopfer et al. | 604/415 |
| 5,226,878 A | * | 7/1993 | Young | 604/89 |
| 5,308,347 A | * | 5/1994 | Sunago et al. | 604/403 |
| 5,342,346 A | * | 8/1994 | Honda et al. | 604/413 |

(Continued)

*Primary Examiner* — Paula L. Craig
(74) *Attorney, Agent, or Firm* — Lucas & Mercanti, LLP

(57) ABSTRACT

The present invention relates to unitary bottle for injection, more particularly, to a unitary medicine bottle having an integral structure where a medicine container is easily connected with a plastic container including a solution at a sterilized state so that powdered, freeze-dried or liquid medicine is mixed with the solution with one touch. The unitary medicine bottle for injection comprises: a plastic container equipped with a coupling member connected with a medicine container at one end and a releasing member for releasing a liquid medicine at the other end; a protection cap integrally formed with the coupling member to accept the medicine container; and a flue needle which moves forward in a direction of the medicine container, perforating a stopper of the medicine container and is inserted in the coupling member connecting the plastic container with the medicine container.

7 Claims, 6 Drawing Sheets

(56) References Cited

U.S. PATENT DOCUMENTS

| | | | |
|---|---|---|---|
| 5,352,191 A * | 10/1994 | Sunago et al. | 604/7 |
| 5,364,386 A * | 11/1994 | Fukuoka et al. | 604/411 |
| 5,380,315 A * | 1/1995 | Isono et al. | 604/416 |
| 5,478,337 A * | 12/1995 | Okamoto et al. | 604/413 |
| 5,826,713 A * | 10/1998 | Sunago et al. | 206/222 |
| 5,827,262 A * | 10/1998 | Neftel et al. | 604/414 |
| 6,071,270 A * | 6/2000 | Fowles et al. | 604/413 |
| 6,875,203 B1 * | 4/2005 | Fowles et al. | 604/403 |
| 8,128,612 B2 * | 3/2012 | Oh | 604/416 |
| 2002/0127150 A1 * | 9/2002 | Sasso | 422/103 |
| 2004/0199139 A1 * | 10/2004 | Fowles et al. | 604/414 |
| 2008/0269712 A1 * | 10/2008 | Oh | 604/411 |

* cited by examiner

INTEGRATED INFUSION CONTAINER

FIELD OF THE PRESENT INVENTION

The present invention relates to a unitary medicine bottle for injection, more particularly, to a unitary medicine bottle having an integral structure where a medicine container is easily connected with a plastic container including a solution at a completely sterilized state so that powdered, freeze-dried or liquid medicine is mixed with the solution with one touch for a short time.

BACKGROUND OF THE PRESENT INVENTION

In general, in order to administer powdered form or lyophilized (powder) form of anticancer medicine or a freeze-dried medicine to a patient in a clinic like a hospital, the powdered medicine included in a container like a vial is mixed with a certain amount of solution, like a saline solution, and then it is instilled.

For instillation, methods for mixing the powdered medicine with a solution are as follows. First, a solution like a saline solution is injected into a vial with a throwaway syringe to dissolve the powered medicine, and the dissolved solution is transferred to the solution container with the throwaway syringe, also. This method is generally used because it does not need additional equipment, but it is disadvantageous in that impurities may be infiltrated and operations are complicated.

Second, the container including the dissolved medicine is coupled with the container including the solution using a coupling tool such as a double-ended needle or a coupling tube. The container including the dissolved medicine is inclined so that the medicine dissolved in the container is inserted into the container including the solution.

However, the above operations are complicated and time-consuming. In particular, as the operation for perforating a hole for connection on a container including a medicine is carried out in the air, the possibility of contaminating the included medicine is increased. Moreover, the possibility of a nosocomial infection due to an abuse of antibiotic injection is increased, also. As a method for solving the above problem, a medicine bottle for injection where a capsule receiving a vial being a medicine container is connected with a plastic container filled with a solution having an outlet of a liquid medicine by a tube has been developed. In the tube, a hollow cavity needle is attached toward the vial and a breaking material like a tube made of plastic is attached toward the plastic container. The breaking material blocks a passage in the tube for holding a liquid from flowing.

When using this, the vial in the capsule is pressed and a rubber stopper is pricked with the cavity needle to connect the plastic container with the vial. The breaking material is broken with a finger for the passage in the tube to be reopened so that the medicine is mixed with the solution. The more improved one than the above medicine bottle for injection includes a plastic container having a liquid passage with an enclosure at the uppermost and filled with a solution or a diluted solution in the medicine bottle for injection, a capsule connected with the plastic container, a medicine container connected by pricking its rubber stopper of which the inlet is closed with a needle and which is maintained in the capsule and a flue means for connecting the inside of the plastic container with the inside of the medicine container.

In addition, the flue means includes a hollow cavity needle having a hub in the middle and blades at both ends, a control means for perforating a stopper of the medicine container by one blade of the cavity needle and an enclosure of the plastic container by the other blade of the cavity needle in a serial order so as to connect the plastic container with the medicine container.

SUMMARY OF THE PRESENT INVENTION

The above described medicine bottle for injection is improved in that a medicine container is connected with a plastic container including a solution, but a plurality of operations that the rubber stopper of a vial is pricked by a cavity needle and a breaking material is broken with a finger to open the passage require quite a long time. Moreover, when the breaking material is incompletely broken, there occur problems that the solution is difficult to pass through the passage and a lot of time for dissolving it is required. The above medicine bottle for injection is considered to be improved in that a medicine is mixed by connecting a medicine container with a plastic container including a solution, and a shortened time consumed for its operation. However, the medicine bottle for injection has a problem that a flue means needs a hollow osteoplastic needle having a hub in the middle and blades at both ends and a complicatedly shaped control means for controlling a connecting order so that one blade of the osteoplastic needle pricks the stopper of a medicine container first and the other blade of it pricks the enclosure of the plastic container. In addition, as the medicine bottle for injection consists of a number of parts, a manufacturing costs is high and the possibility of malfunctions is increased.

In addition, there present various sizes of medicine containers. The conventional medicine bottles for injection were manufactured in accordance with the size of each medicine container. Therefore, it is disadvantageous in that the manufacturing cost is increased because a molding die must be manufactured for producing medicine bottle for injections corresponding to the sizes of various medicine containers.

DETAILED DESCRIPTION OF THE PREFERRED EMBODIMENT

Best Mode for Carrying Out the Invention

In order to obtain the above objects, it is an object of the present invention is to provide a unitary medicine bottle for injection comprising: a plastic container having a coupling member to be connected with a medicine container at one end and a releasing member for releasing a liquid medicine to be injected at the other end; a protection cap integrally formed with the coupling member to accept the medicine container; and a flue needle which moves forward in a direction of the medicine container and perforates a stopper of the medicine container and is inserted into the coupling member connecting the plastic container with the medicine container. The coupling member is characterized by comprising a guide section for guiding the flue needle and a diaphragm for supporting in contact with the stopper of the medicine bottle.

In addition, the coupling member is characterized by comprising a stopper for limiting forward movements of the flue needle. Moreover, the protection cap is characterized by comprising a fixing cap which is one body with the coupling member, a moving cap which is interpolated or extrapolated in the fixing cap for changing its inner space and a moving flange which is integrally formed with the fixing flange at an end of the fixing cap and fixed on the moving cap to set a space for forming the moving cap and the fixing cap. In addition, the protection cap is characterized by comprising a fixing packing for holding the medicine container to be fixed. Moreover, the protection cap is characterized by comprising a hanging means for hanging a medicine bottle.

In addition, the flue needle is a cavity needle having at least one passage through which a liquid medicine flows. Moreover, the flue needle is characterized in that an interrupting protuberance is formed at one side so that it stops at a predetermined position in the coupling member after it moved not to be displaced further.

Moreover, the flue needle is characterized in that an interrupting protuberance is formed at a side so that it is not easily displaced from the initial state without an external force. In addition, the medicine container is formed of a glass or a plastic. Moreover, the stopper of the medicine container is formed of rubber or plastic. In addition, the releasing member is characterized by comprising: an outlet fixed to the plastic container so that a liquid medicine is not leaked; a releasing extended rim mounted at an inner end of the outlet; a releasing cap covering the end of the outlet to expose only the center of the releasing extended rim; and a cover seal attached to the outside of the releasing cap for sealing the releasing extended rim. Moreover, the connection between a moving flange and a fixing flange, and the connection between the moving flange and the moving cap are made by a thermal fusion, a supersonic fusion or a sealing bending.

Mode for the Invention

Figure 1:
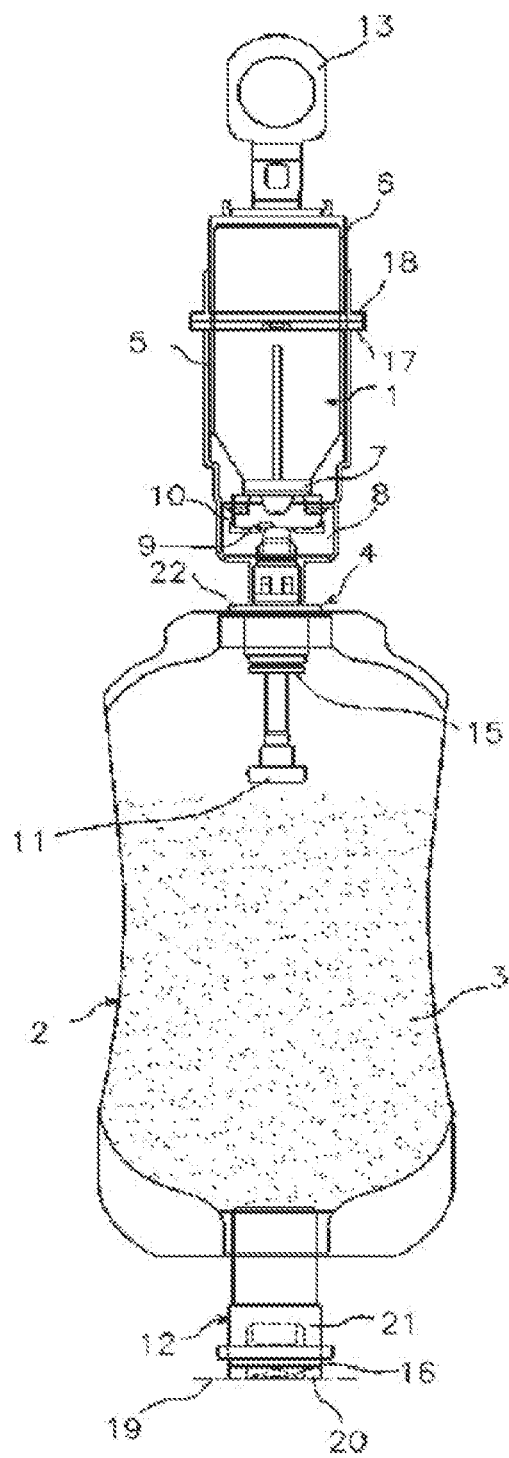
FIG. 1 is a configurational view of a unitary medicine bottle for injection in accordance with the present invention.

FIG. 1 shows a unitary medicine bottle in accordance with the present invention, consisting of a plastic container (2), a protecting cap, a releasing member, a flue needle (11), the protecting cap being inserted by a medicine container (1). The medicine container (1) is disclosed and is formed of plastic or glass. The medicine container (1) has a neck (7) at which a stopper (10) is formed to seal the contained medicine.

Figure 2:
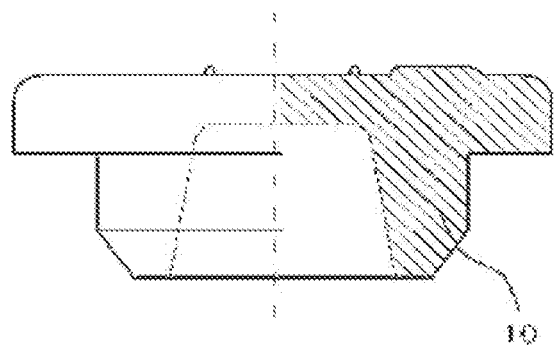
FIG. 2 is a cross-section of a stopper of a liquid medicine container.

Moreover, the stopper (10) is hermetically sealed at the neck (7) of the medicine container (1) by an aluminum cover (not shown). Accordingly, the medicine filled in the medicine container (1) is protected at a completely sterilized state. The stopper (10) is inserted in the packing (8) to be conjugated between the medicine container (1) and the coupling member (4) in an aseptic condition. The stopper (10) is formed of rubber or plastic to have the same shape shown in FIG. 2.

The medicine included in the medicine container is used by pricking the stopper (10) with an injection needle or a flue needle of a medicine bottle, etc. The medicine in the medicine container is in a liquid or powdered state. The powdered medicine is dissolved to be used.

The medicine inserted into the medicine container (1) includes cephem series pre-antibiotics like Cefazolin Sodium, ceftizoxime sodium, Cefotiam HCL etc., penicillin series antibiotics like Ampicillin Sodium and penicillin soldium etc., carbapenum series antibiotics like imipenem, various antibiotics like mitomycine C and fluorourcil, anti-ulcer agents like Famotidine and hydrochloric acid Ranitidine, a thrombosis solvent like urokinase and flomoxef sodium.

The plastic container (2) is a synthetic resin pack used to contain a solution (3) like saline solution and may be formed of a material with affluent plasticity such as a low density polyethylene resin, a linear low density polyethylene resin, polypropylene resin, soft polyethylene resin, chlorinated polyethylene resin, chlorinated vinyl resin and ethylene acetic acid vinyl copolymer.

It is preferable to use a polyolefin series resin like a low density polyethylene resin, a linear low density polyethylene resin and polypropylene resin because they are chemical resistant, has small effluents and cost-effective. The solutions to be contained in the plastic container (2) include solution including various electrolytes besides a saline solution, 5% dextrose solution and distilled water for injection.

Figure 3:
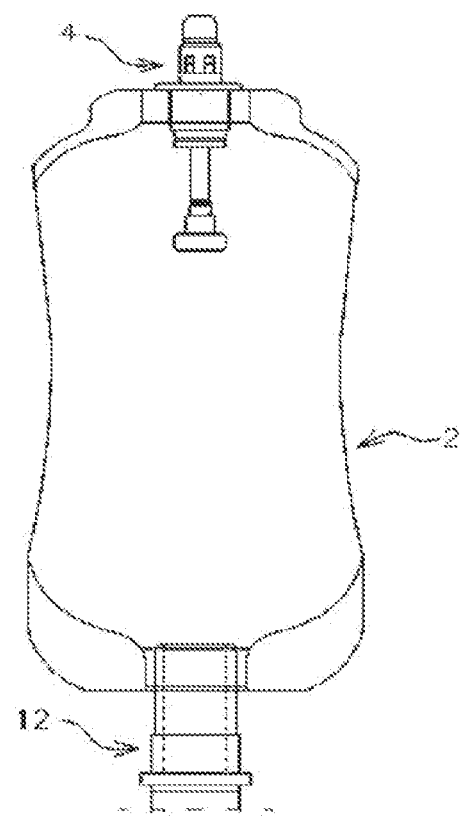
FIG. 3 is a configurational view of a plastic container shown in FIG. 1.
Figure 4:
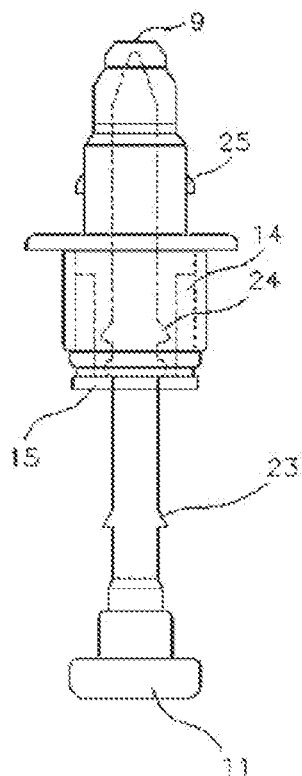
FIG. 4 is a partial exploded view of a coupling member and a flue needle shown in FIG. 1.
Figure 5:
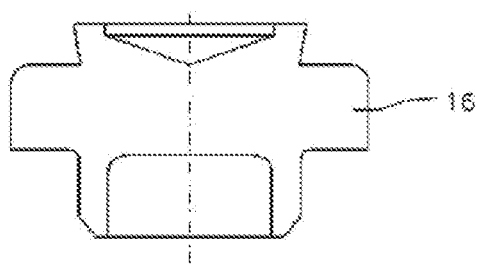
FIG. 5 is a cross-section of a releasing extended rim.

As shown in FIG. 3, the plastic container (2) is equipped with a coupling member (4) connected with the medicine container (1) at one end and a releasing member (12) for releasing the liquid medicine to be injected at the other end. The coupling member (4) and the releasing member (12) are attached to the plastic container (2) by a thermal fusion so that the solution is not leaked. As shown in FIG. 4, the coupling member (4) comprises a guide section (14) for guiding the flue needle (11) and a diaphragm (9) for supporting a stopper (10) of the medicine container (1). In addition, a flange (22) formed at the side of the coupling member (4) is used together with the seats of the flue needle (11) with the same method as injecting a liquid medicine. In other words, the flue needle (11) is pushed upward by pressing the seats with a thumb and placing an index finger and a middle finger on the flange (22).

A pipe is formed inside the coupling member (4) so that the flue needle (11) can make linear movements and an annular conjugation protuberance (25) is formed at an outer end so that the packing (8) is integrally sealed with the coupling member (4). The diaphragm (9) of the coupling member (4) is formed in a dome to be closely adhered to a central portion of the stopper (10) of the medicine container (1). Moreover, the diaphragm (9) has a thin layer which is easily perforated by the flue needle (11). If it is blocked, it plays a role in sealing the plastic container (2). In addition, a stopper (15) is formed at the bottom of the coupling member (4) to play a role in limiting a vertical movement distance of the flue needle (11).

The flue needle (11) inserted in the coupling member (4) is a cavity needle with at least one passageway through which a liquid medicine flows, having the similar shape to a general injection syringe. The flue needle (11) has a seat which is pressed by a finger at one end. The flue needle (11) has a fixing protuberance (24) so that the flue needle (11) is not easily displaced from the initial state and an interrupting protuberance (23) at one side so that the flue needle (11) is stopped at a predetermined position inside the coupling member (4) and not to be displaced further.

Accordingly, if the flue needle (11) is not applied by an external force from the fixing protuberance (24) at the initial state, it is not displaced. If the flue needle (11) is applied by an external force, it is moved toward the diaphragm (9) along with the guide section (14) and displaced by a predetermined distance and is stopped by the interrupting protuberance (23) and/or the stopper (15). Therefore, the flue needle (11) moves forward and pricks the stopper (10) of the medicine container (1) and plays a role in connecting the inside of the medicine container (1) with the inside of the plastic container (2), maintaining the state that the stopper is perforated. The releasing member (12) consists of an outlet (21) which is closely attached with the plastic container (2) so that a liquid medicine is not leaked, a releasing extended rim (16) which is mounted inside an end of the outlet (21), a releasing cap (20) for exposing only the center of the releasing extended rim (16) by covering one end of the outlet (20) and a cover seal (19) attached to the outside of the releasing cap (20) to seal the releasing extended rim (16). The outlet (21) is thermally fused with the plastic container (2) to be sealed. The releasing extended rim (16) made of a rubber, etc. (shown in FIG. 6) is forced to place inside of the outlet (21).

Figure 6:
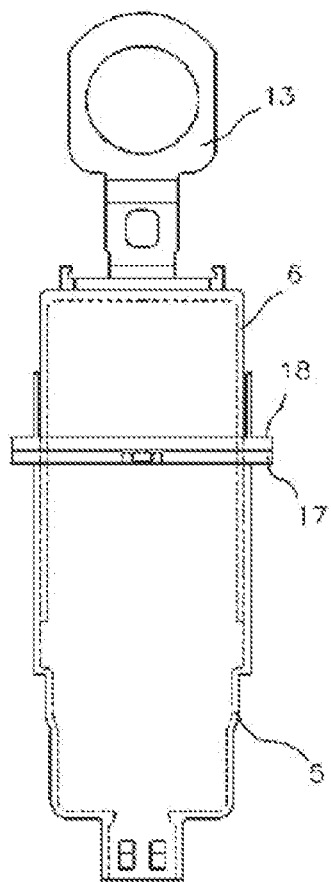
FIG. 6 is an exploded view of a protection cap.

The cover seal (19) is attached to the outside of the releasing cap (20) by a thermal fusion or a supersonic fusion. Therefore, the medicine bottle for injection according to the present invention can be sealed at an aseptic state by attaching the cover seal (19). The protection cap is integrally formed with the coupling member (4) to include a medicine container (1). Especially, as shown in FIG. 6, the protection cap includes a fixing cap (5) integrally formed with the coupling member (4), a moving cap (6) which is interpolated or extrapolated in the fixing cap (5) to change the integral space, and a moving flange (18) which is integrally connected with the fixing flange (17) formed at one end of the fixing cap (5) and fixed to the moving cap (6) to set a space formed by the moving cap (6) and the fixing cap (5).

The connection with the moving flange (18) and the fixing flange (17) and the connection with the moving flange (18) and the moving cap (6) are carried out by a thermal fusion or a supersonic fusion. The size of the internal space formed by the moving cap (6) and the fixing cap (5) is not limited, thus all sizes of medicine container (1) can use it. The medicine container (1) mounted in the internal space formed by the moving cap (6) and the fixing cap (5) is protected from the external impact. The medicine container (1) is mounted with the stopper (10) inserted in the packing (8) mounted inside the fixing cap (5), upside down.

Figure 7:
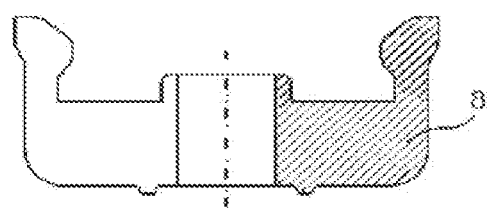
FIG. 7 is a cross-section of a packing.

As shown in FIG. 7, the packing (8) is formed to wrap the stopper (10) and has a hole in the center so that the diaphragm (9) of the coupling member (4) is inserted. The fixing cap (5) and the moving cap (6) are formed of a polyolefin series resin, a stylene series resin, an acryl series resin, a polycarbonate resin, polyamide resin, etc.

The fixing cap (5) and the moving cap (6) can sterilize their insides easily by a λ-ray and a ultraviolet ray or a peroxide processing, using a polypropylene resin which relatively penetrates an ultraviolet ray and a methylpentene resin. A hanging means (13) has a hook or a hanging hole formed at the upper side of the moving cap (6), thus an unitary medicine bottle according to the present invention is hung on a hanger to be stably kept. The operating methods according to the present invention now will be described.

Figure 8:
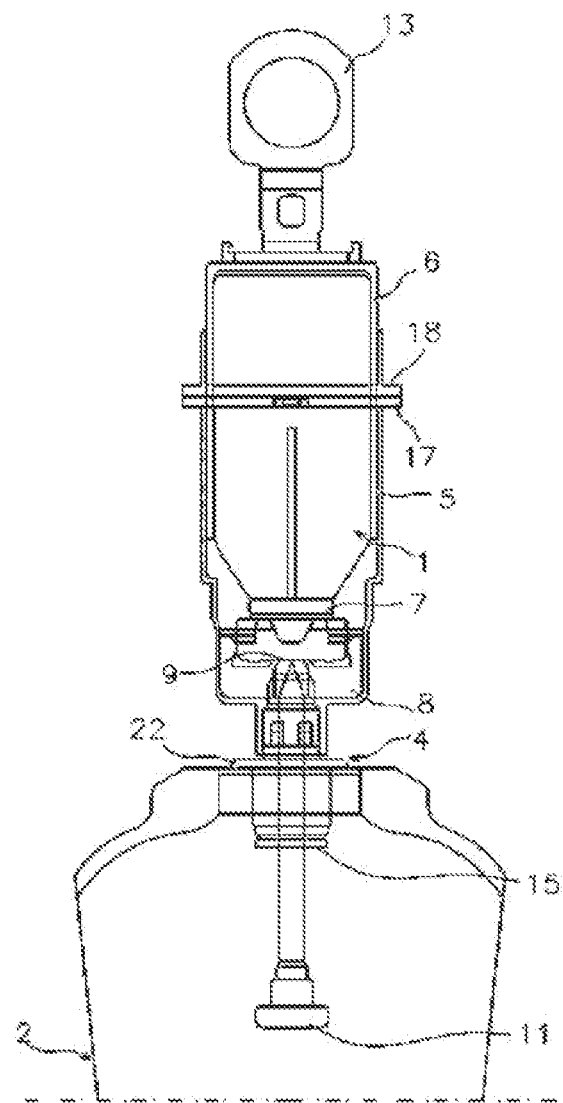
FIG. 8 is a partially exploded view of an initial state of an embodiment.
Figure 9:
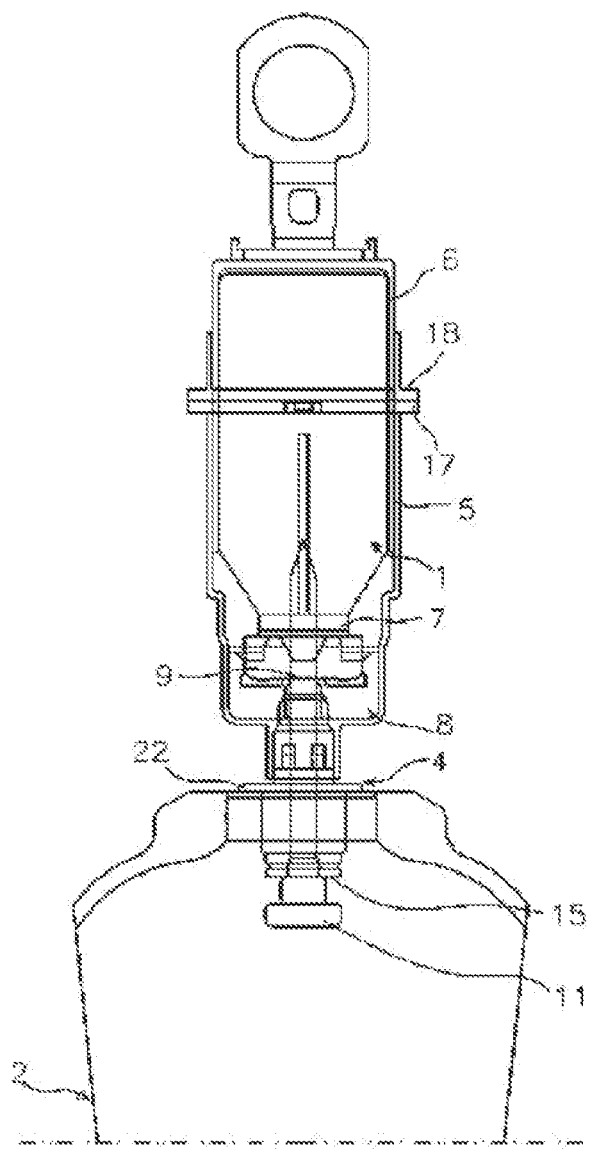
FIG. 9 is a partially exploded view of a displaced flue needle of an embodiment.

First, the flue needle (11) is moved vertically from the outside of the plastic container (2) shown in FIG. 8 by pressing it toward the diaphragm (9) of the coupling member (4), as shown in FIG. 9 The front end of the flue needle (11) is guided to the guide section (14) to penetrate the diaphragm (9) of the coupling member (4). As the front end of the penetrated flue needle (11) penetrates the stopper (10) of the medicine container (1) and the flue needle (11) goes inside the medicine container (1), the inside of the medicine container (1) and the inside of the plastic container (2) are connected by a flue needle being a cavity needle. After the inside of medicine container (1) in connected with the inside of the plastic container (2), the plastic container (2) is pressurized with both hands slightly to send a part of solution into the medicine container (1), thus dissolving the medicine. In addition, a unitary medicine bottle for injection is shaken a few times so that the medicine in the medicine container (1) is dissolved fast. Next, the liquid medicine dissolved in the medicine container (1) is returned back to the plastic container (2) by the operations of pressurizing or pressing the plastic container (2). The liquid medicine including the liquid medicine and the solution (3) which are mixed in the plastic container (2) is released from the releasing means (12) attached at one end of the plastic container (2). At this time, the cover seal (19) is removed from the releasing cap (20) and a set of medicine bottle for injection is coupled to the releasing extended rim (16), thus a liquid medicine is instilled.

The foregoing embodiments are merely exemplary and are not to be construed as limiting the present invention. The description of the present invention is intended to be illustrative, and not to limit the scope of the claims. Many alternatives, modifications and variations will be apparent to those skilled in the art within the scope of the invention.

INDUSTRIAL APPLICABILITY

As described above, the unitary medicine bottle for injection according to the present invention does not move a medicine container and a plastic container each other. Therefore, as the medicine bottle is compact and the number of constitutional parts is small, it is possible to manufacture the unitary medicine bottle for injection easily and cost-effectively.

I claim:

1. A unitary medicine bottle for injection comprising:
a coupling member;
a plastic container at a first end of the coupling member;
a medicine container at a second end of the coupling member;
a cap connected to the second end of the coupling member to accept the medicine container;
a flue needle;
a flange; and
a releasing member,
wherein,
the plastic container has a first end and a second end, the coupling member is at the first end of the plastic container, the releasing member is at the second end of the plastic container, and the first end of the plastic container is opposite the second end of the plastic container;
the medicine container is penetrable;
the cap comprises:
a fixing cap which is one body with the coupling member;
a moving cap interpolated within the fixing cap for altering the size of an aseptic interior space when the moving cap moves;
the flue needle is inserted into the coupling member, and the coupling member is fixed in reference to the plastic container and in reference to the fixing cap, wherein the flue needle moves towards the medicine container, penetrating the medicine container independently of the medicine container;

the medicine container is equipped with a stopper configured to be penetrated by the flue needle; and the flange comprises:
- a fixing flange; and
- a moving flange;
    wherein the moving flange and the fixing flange are aligned with each other and conform to each other at an end of the fixing cap, and the moving flange is attached to the moving cap and the fixing flange is fixed on the fixing cap to set the aseptic interior space; and
    the coupling member and the stopper are in direct contact when the stopper is pierced.

2. The unitary medicine bottle for injection of claim 1, wherein the medicine container is mounted to be inverted with the stopper within the fixing cap.

3. The unitary medicine bottle for injection of claim 1, wherein the coupling member remains intact while piercing the stopper.

4. The unitary medicine bottle for injection of claim 1, wherein the cap is configured to be sized for the medicine container.

5. The unitary medicine bottle for injection of claim 1, wherein the cap is configured to extend and contract in length.

6. The unitary medicine bottle for injection of claim 1, wherein the coupling member contains the flue needle tip outside the plastic container while holding the flue needle away from the medicine container.

7. The unitary medicine bottle for injection of claim 1, wherein
    the coupling member holds the medicine container in-line and with the stopper opposing the flue needle tip,
        wherein the flue needle tip disposed adjacent to the plastic container, and the flue needle is covered with an enclosure.

* * * * *